US011872142B2

(12) United States Patent
Basta et al.

(10) Patent No.: US 11,872,142 B2
(45) Date of Patent: Jan. 16, 2024

(54) GAP BALANCING ASSEMBLY FOR KNEE REVISION SURGERY

(71) Applicant: ORTHOSOFT ULC, Montreal (CA)

(72) Inventors: Ian Basta, Montreal (CA); Bahareh Khatibi, Montreal (CA); Jeremie Menard, Montreal (CA)

(73) Assignee: ORTHOSOFT ULC, Montreal (CA)

( * ) Notice: Subject to any disclaimer, the term of this patent is extended or adjusted under 35 U.S.C. 154(b) by 64 days.

(21) Appl. No.: 17/331,844

(22) Filed: May 27, 2021

(65) Prior Publication Data

US 2021/0369470 A1 Dec. 2, 2021

Related U.S. Application Data

(60) Provisional application No. 63/031,313, filed on May 28, 2020.

(51) Int. Cl.
*A61F 2/46* (2006.01)
*A61B 17/17* (2006.01)

(52) U.S. Cl.
CPC .......... *A61F 2/461* (2013.01); *A61B 17/1764* (2013.01); *A61F 2002/4687* (2013.01)

(58) Field of Classification Search
CPC ................................................. A61B 17/1764
See application file for complete search history.

(56) References Cited

U.S. PATENT DOCUMENTS

2019/0046217 A1* 2/2019 Rasmussen ........ A61B 17/1764
2019/0274696 A1* 9/2019 Goble .................. A61B 17/155

* cited by examiner

*Primary Examiner* — Sameh R Boles
(74) *Attorney, Agent, or Firm* — NORTON ROSE FULBRIGHT CANADA LLP

(57) ABSTRACT

A gap balancing assembly includes an alignment plateau adapted to abut against an articular surface of a first bone, and at least one gap spacer portion adapted to space the articular surface from a second bone, the at least one gap spacer portion having a thickness profile. A spacer member has a first contact surface for being abutted against said tibial alignment plateau, and a second contact surface oriented and spaced relative to the first contact surface to correspond to the thickness profile of the at least one gap spacer portion, the second contact surface adapted to contact a cut guide to align same with the articular surface of the first bone.

17 Claims, 5 Drawing Sheets

GAP BALANCING ASSEMBLY FOR KNEE REVISION SURGERY

CROSS-REFERENCE TO RELATED APPLICATION

The present application claims the benefit of U.S. Patent Application No. 63/031,313, filed on May 28, 2020, the contents of which are incorporated herein by reference.

TECHNICAL FIELD

The present disclosure relates to total knee replacement in orthopedic surgery and in particular to tools assisting in soft tissue balancing in knee revision surgery.

BACKGROUND

In the context of a total knee replacement, over time, it may be necessary to perform knee revision surgery. Indeed, the tibial component and/or the femoral component may become worn. Revision surgery entails that implants are removed and replaced by new ones.

However, there are challenges with such surgeries. As revision surgery involves the replacement of the implants and the incident removal of bone, there may be a variation in the geometry of the knee joint. The knee is known to be a complex anatomic joint in which the tibia and the femur move between flexion and extension while supporting the load of the body. Ligaments interrelate the femur to the tibia to ensure that the bones are stable relative to one another. The revision of implants may have an impact on the tension of the ligaments, and other soft tissue. Ultimately, an unbalance in the soft tissue may affect the stability of the knee, cause discomfort, and provoke injury.

SUMMARY

In one aspect, there is provided a gap balancing assembly comprising: a tibial alignment plateau adapted to abut against an articular surface of the tibia, and at least one gap spacer portion adapted to space the articular surface from a femur, the at least one gap spacer portion having a thickness profile, and a spacer member having a first contact surface for being abutted against said tibial alignment plateau, and a second contact surface oriented and spaced relative to the first contact surface to correspond to the thickness profile of the at least one gap spacer portion, the second contact surface adapted to contact a femoral cut guide to align same with the articular surface of the tibia.

In another aspect, there is provided a method for orienting a femoral cut guide comprising: abutting a tibial alignment plateau against an articular surface of a tibia; spacing a femur from the tibial alignment plateau using at least one gap spacer portion having a thickness profile to achieve a desired soft tissue balance, the desired soft tissue balance being indicative of a desired transepicondylar axis; and orienting a femoral cut guide to the desired transepicondylar axis as a function of the thickness profile.

In another aspect, there is a gap balancing assembly comprising: an alignment plateau adapted to abut against an articular surface of a first bone, and at least one gap spacer portion adapted to space the articular surface from a second bone, the at least one gap spacer portion having a thickness profile, and a spacer member having a first contact surface for being abutted against said tibial alignment plateau, and a second contact surface oriented and spaced relative to the first contact surface to correspond to the thickness profile of the at least one gap spacer portion, the second contact surface adapted to contact a cut guide to align same with the articular surface of the first bone.

DESCRIPTION OF THE DRAWINGS

Reference is now made to the accompanying figures in which.

DETAILED DESCRIPTION

Figure 1:
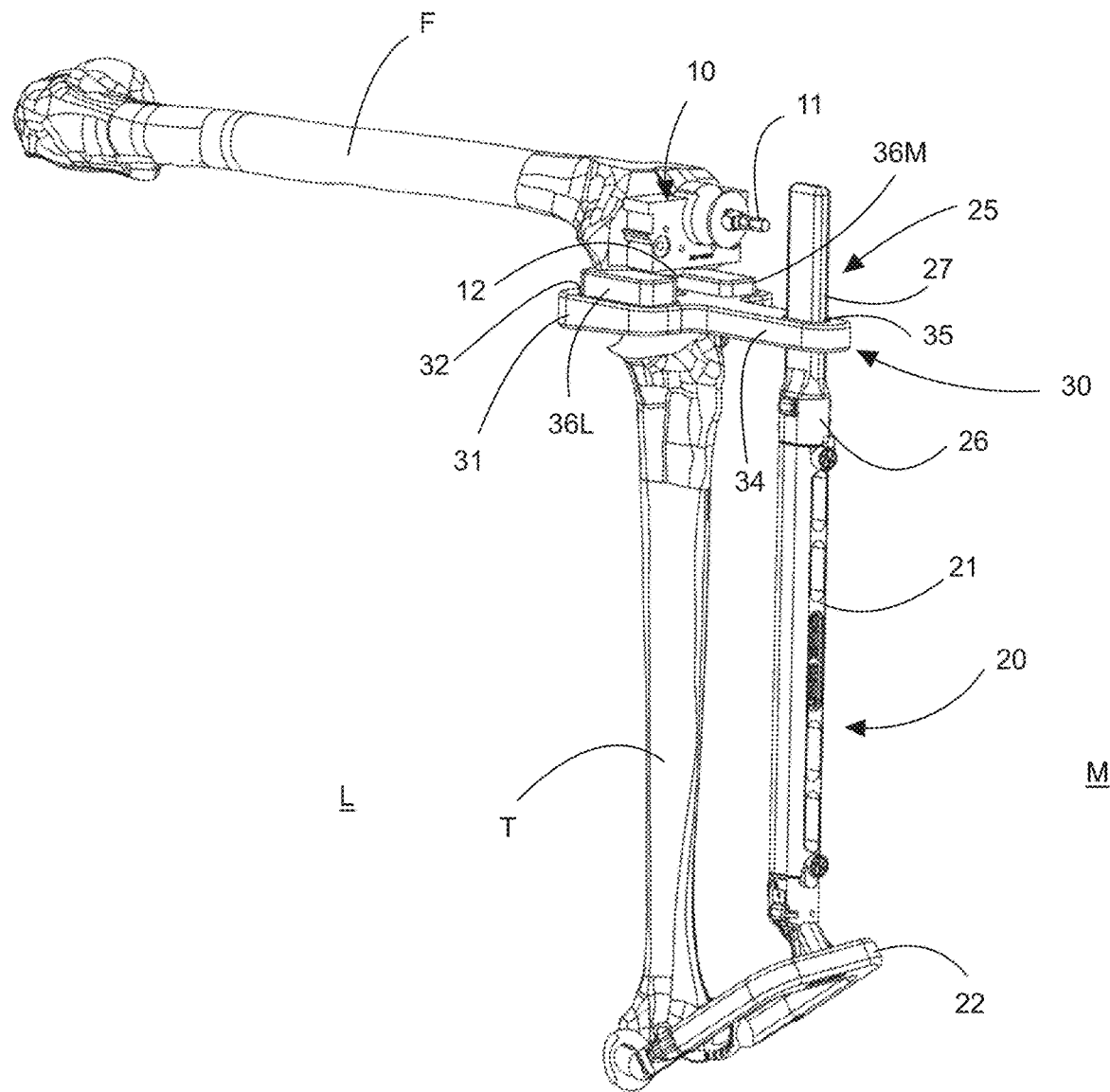
FIG. 1 is a perspective view of a leg with a gap balancing assembly of the present disclosure.
Figure 2:
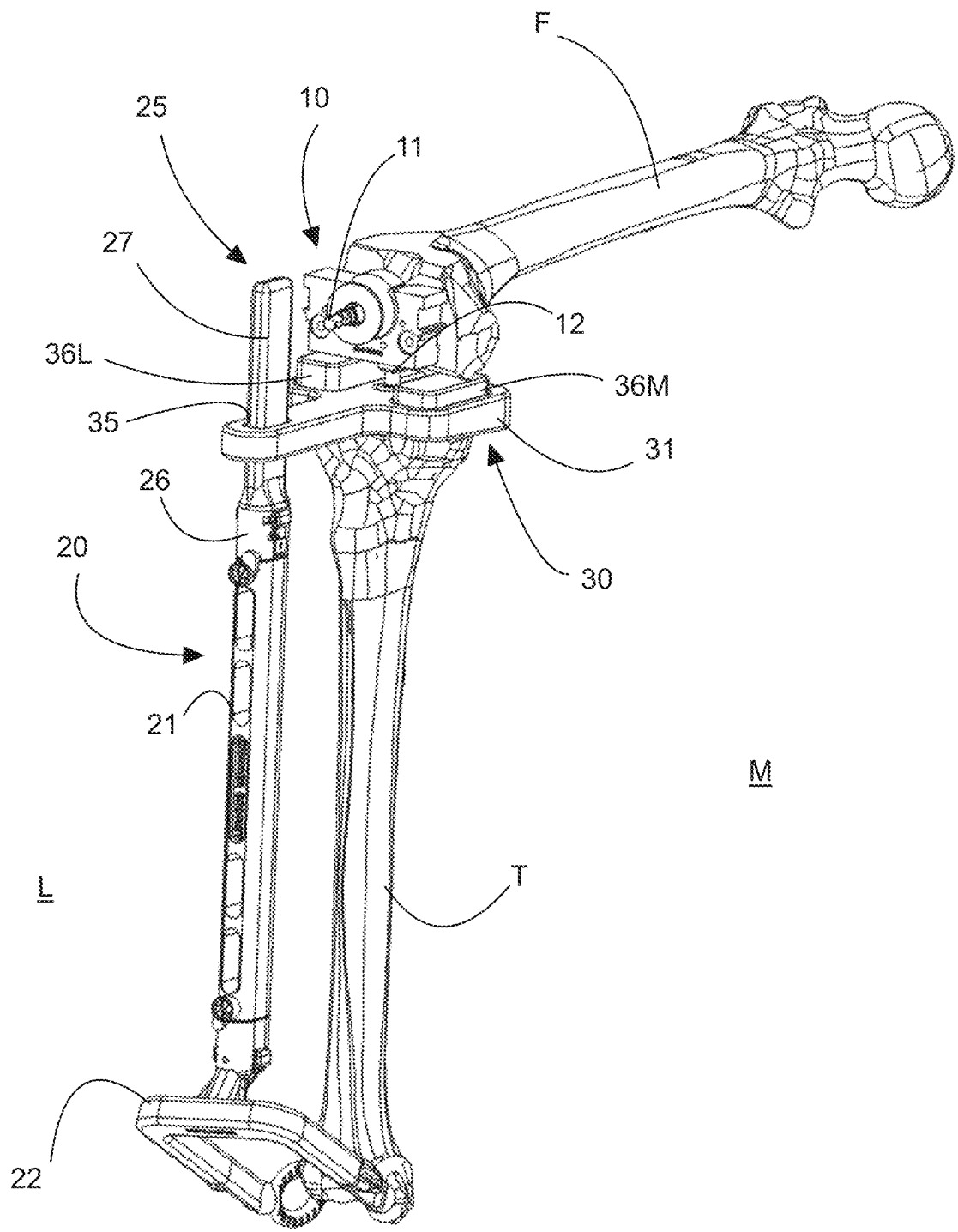
FIG. 2 is another perspective view of the leg with the gap balancing assembly of FIG. 1.

Referring to the drawings and more particularly to FIGS. 1 and 2, there is illustrated a femur F relative to a tibia T. For simplicity, and to illustrate the interaction between the tools and the bones, bones models are shown without soft tissue. It is understood that in a context of surgery, only a limited portion of the knee joint is exposed while the rest of the bones is covered by soft tissue, including skin, muscles, ligaments, tendons, etc. The present disclosure describes herein a gap balancing assembly that may for instance be used in knee revision surgery, in which one or both the tibial and femoral components of a knee implant are removed for revised implants to be implanted. In FIGS. 1 and 2, the femur F and the tibia T are already operatively removed of implants, namely the tibial component (a.k.a., tibial base plate, tibial implant, tibial plateau, etc) and the femoral component (a.k.a., femoral implant), in the context of revision surgery. Stated differently, the implants have been removed and the bone may have been partially resurfaced. Moreover, as observed, the femur F and the tibia T do not have a native aspect in that they were resurfaced for receiving implants and may have further been damaged and/or altered by the removal of the implants. The femur F and the tibia T may have generally planar surfaces in that such surfaces may have been machined by the removal of the implants and/or by a subsequent step of resurfacing.

A femoral cut guide can as shown as being rotatively mounted to an intramedullary femoral rod 11, or like pin inserted into the femur F, in the intramedullary canal, in a central position, or in any other suitable location. As observed, a joint is present between the cut guide 10 and the intramedullary femoral rod 11 to allow at least one rotational degree of freedom therebetween. As observed from FIG. 2, an intramedullary tibial rod 12 may project upwardly from the tibia or like pin inserted into the tibia T, in the intramedullary canal, in a central position, or in any other suitable location. The intramedullary femoral rod 11 and the intramedullary tibial rod 12 may be inserted in the intramedullary canals of the femur F and of the tibia T, respectively. Although not shown, these rods 11 and 12 may have a reamer portion that has been drilled into an intramedullary canal, for penetration. At the end of surgery, these rods 11 and 12 are typically removed. The femoral cut guide 10 is used as a guide for further resecting surfaces of the femur F, for the implanting of the revised implant. However, in the condition of FIGS. 1 and 2, it may not be properly oriented with the femur F. The present disclosure pertains to a gap balancing assembly by which the femoral cut guide 10 will have its orientation adjusted relative to the femur F once a soft tissue balancing step has been performed, for subsequent resection of the femur F and placement of the revised implant.

According to an embodiment, the gap balancing assembly may include a tibial alignment guide 20, a tibial alignment plateau 30, and/or a cut guide alignment spacer 40. The tibial alignment guide 20 may be used to obtain a reference to a mechanical axis of the tibia T. The tibial alignment plateau 30 may be indicative of a position and/or orientation of the tibial component of the knee implant. The cut guide alignment spacer 40 may be used to adjust an orientation of the femur relative to the position and/or orientation of the tibial component of the knee implant. Other components, such as some described herein, may be part of the gap balancing assembly, or the tibial alignment guide 20, the tibial alignment plateau 30, and/or the cut guide alignment spacer 40 may be combined in a single piece or two-piece assembly. The alignment guide 20 is described for use as applied to the tibia, but as explained herein, it may be applied against the femur or to another bone, for a cut guide to then be used to perform a cut on the tibia. For simplicity, reference is made herein to the tibial alignment guide 20 and the tibial alignment plateau 30, but these devices can be used for other bones.

The tibial alignment guide 20 may have been used in prior steps of the revision procedure, such as to perform cuts on the tibia T. For example, part of the tibia alignment guide 20 may be as described in U.S. Patent Application Publication No. 2018/0353192, filed on Jun. 13, 2018, and incorporated herein by reference. According to an embodiment, the tibial alignment guide 20 has a rod 21. The rod 21 is designed so as to generally be parallel to the mechanical axis of the tibia T. The rod 21 may thus be used as a landmark indicative of the orientation of the tibia T (e.g., the mechanical axis of the tibia), while other orientations are possible as well. For example, the intramedullary tibial rod 12 may have been inserted through the guidance of the tibial alignment guide 20. The rod 21 may have a patient-specific length determined in preoperative planning.

The exemplary parallel relation may be achieved by way of the malleolus clamp 22. The malleolus clamp 22 is designed to clamp against the malleoli. As shown in FIGS. 1 and 2, the clamping action may be done non-invasively, as the malleolus clamp 22 may have discs 22A that abut against the malleoli, in a pre-defined manner. The clamp 22 may have a general U-shaped structure 22B with the discs 22A at its free ends. In a variant, the discs 22A may be brought toward one another by a telescopic joint, for example. A joint 22C may join the clamp 22 to the rod 21, with additional degrees of freedom being possible. In an embodiment, the tibial alignment guide 20 is made in a patient specific manner. More particularly, the tibial alignment guide 20 may have been fabricated based on preoperative planning using appropriate imagery to create 3D models of the tibia. The preoperative planning may be done ahead of the surgical procedure. One contemplated technique for creating the 3D model of the tibia and/or the femur is as described in U.S. Pat. No. 10,881,416, incorporated herein as reference. The malleolus clamps 22 may be sized and/or may include a centering mechanism to position themselves in the preoperative planning. In another embodiment, the tibial alignment guide 20 may have its own implements in order to align itself with the mechanical axis of the tibia T. Reference is made again to U.S. Patent Application Publication No. 2018/0353192 therefor.

Figure 3:
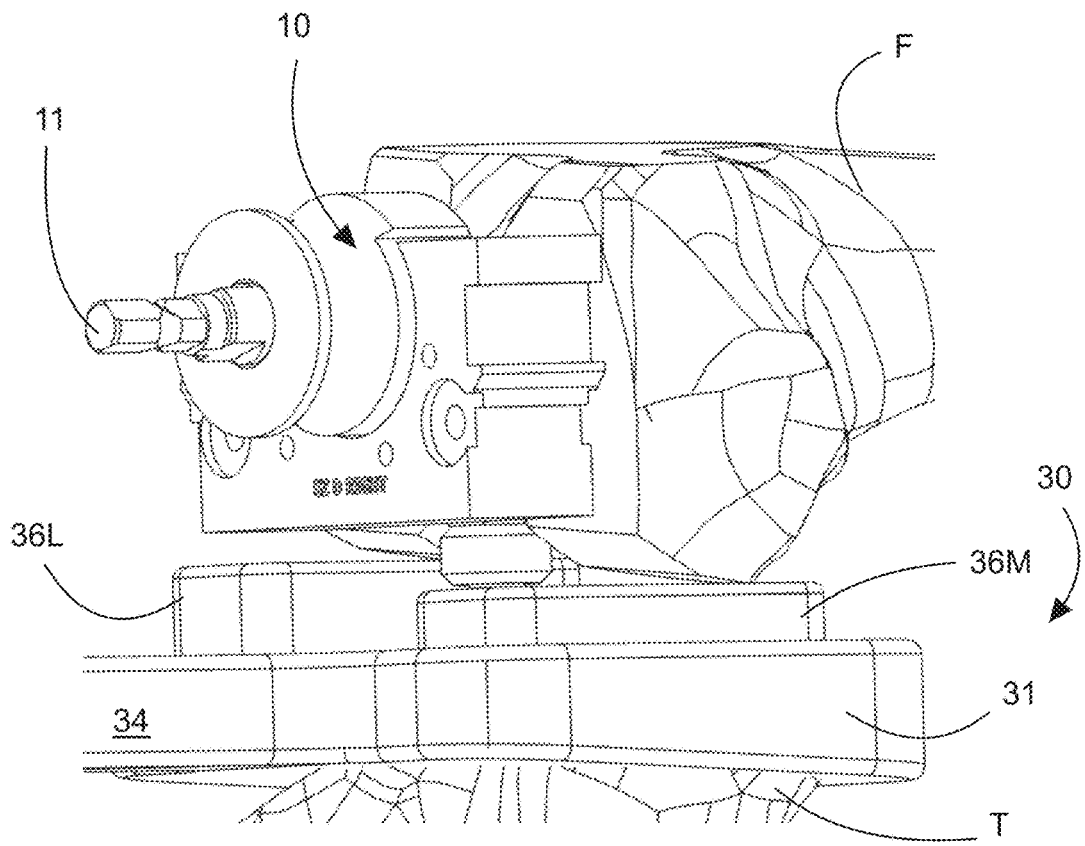
FIG. 3 is an enlarged elevation view of part of the gap balancing assembly relative to a femoral cut guide.
Figure 4:
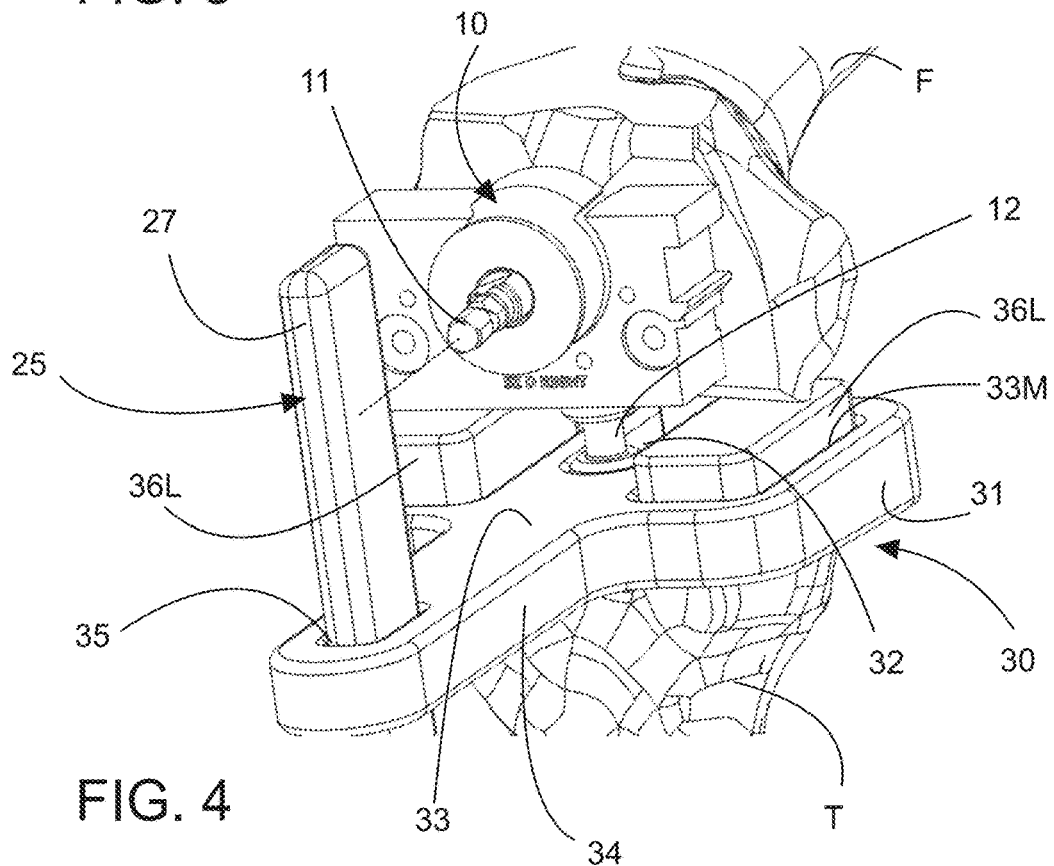
FIG. 4 is a perspective view of the gap balancing assembly relative to the femoral cut guide as in FIG. 3.
Figure 5:
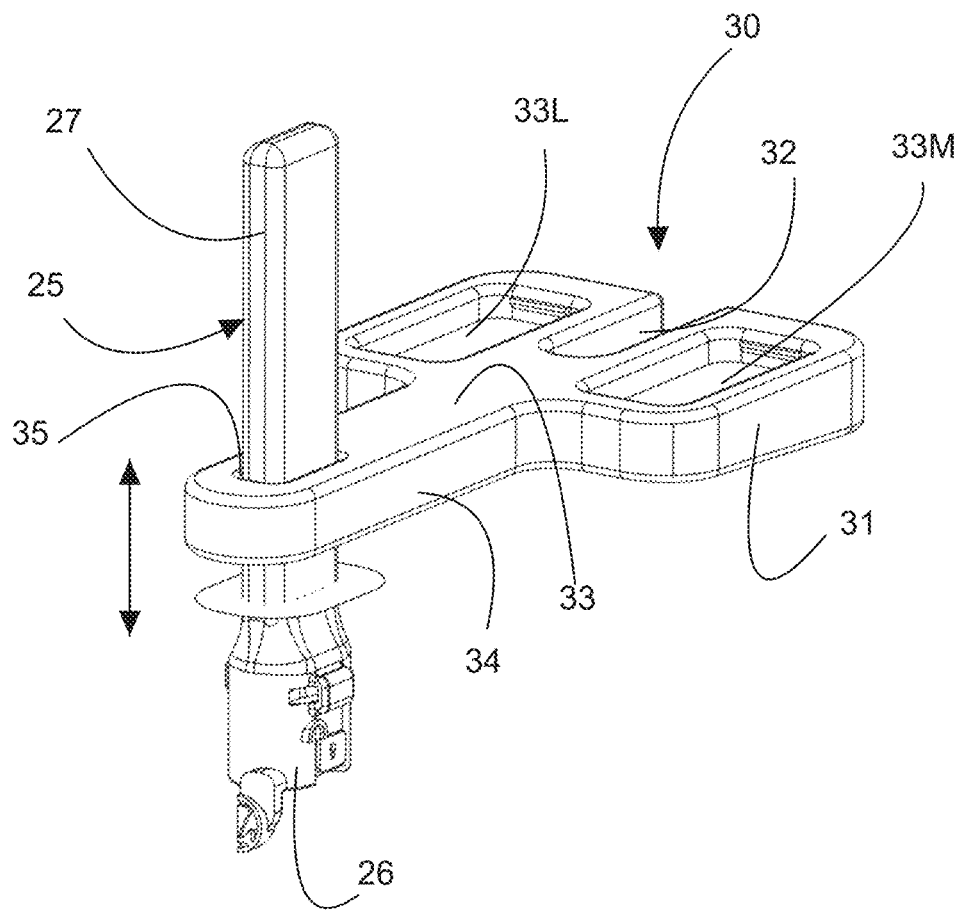
FIG. 5 is a perspective view a tibial alignment plateau of the gap balancing assembly of FIG. 1 as mounted to a slider guide.
Figure 6:
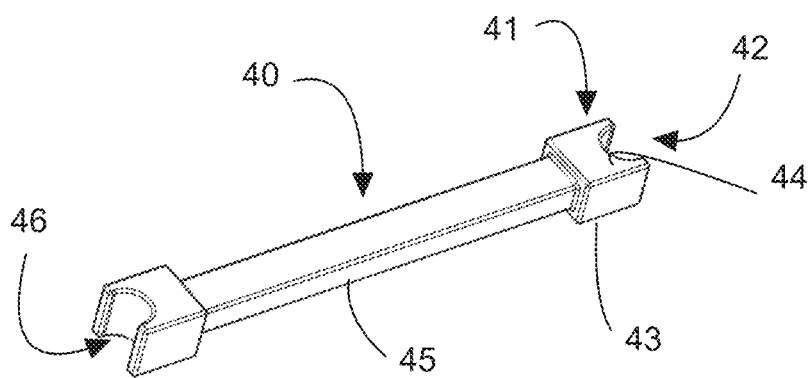
FIG. 6 is a perspective view of a cut guide alignment spacer of the gap balancing assembly.
Figure 7A:
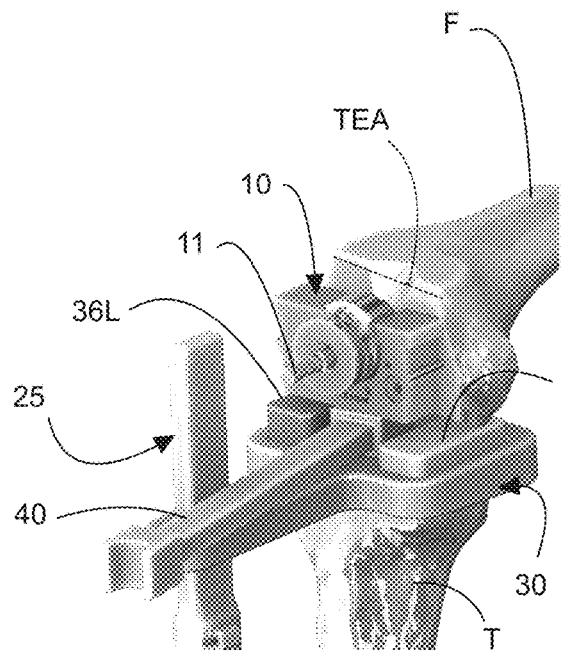
FIGS. 7A-7D are a series of views showing different gap spacer sizes in the tibial alignment plateau along with different sizes of the cut guide alignment spacer.
Figure 7B:
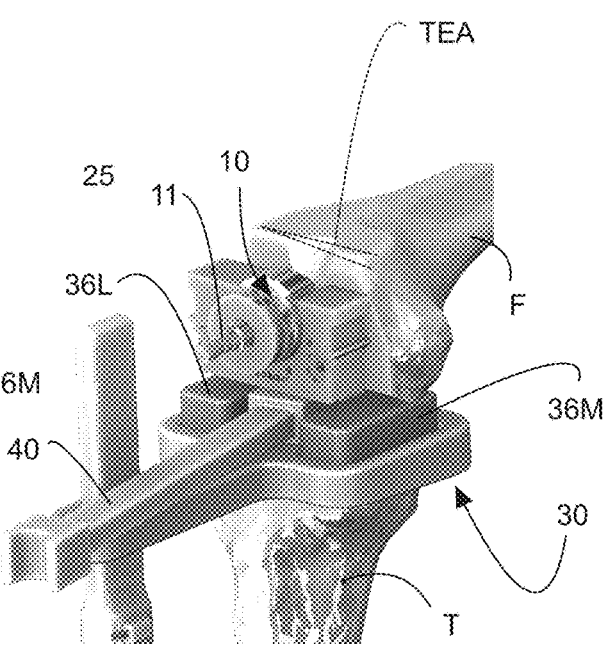
Figure 7C:
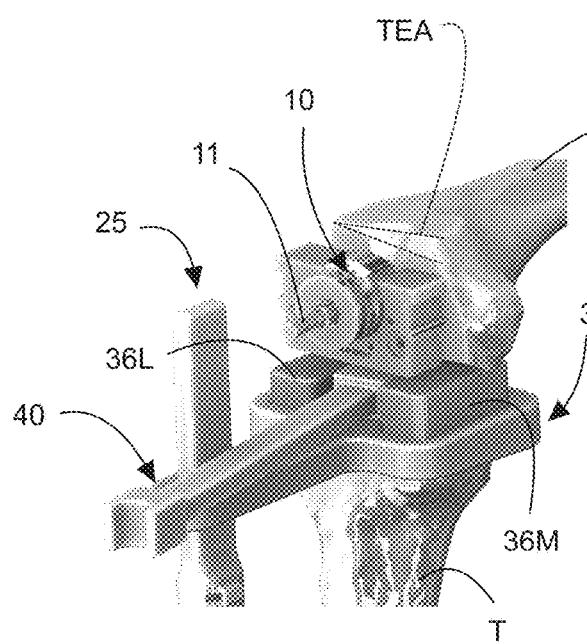
Figure 7D:
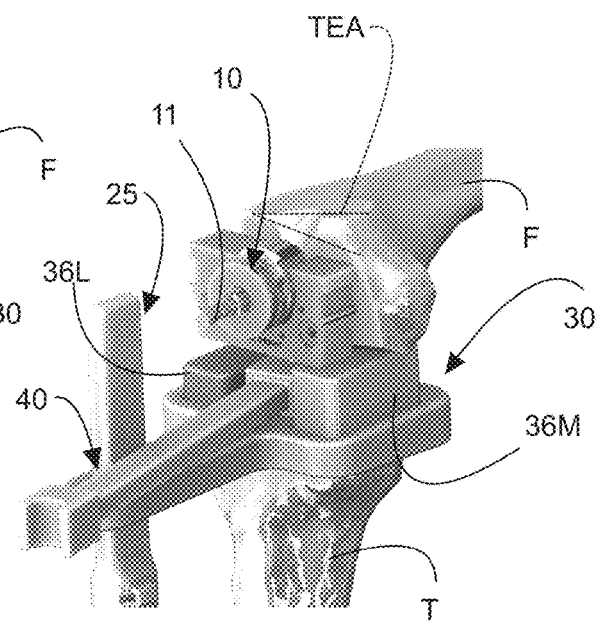

A slider guide 25 may be at the end of the tibial alignment guide 20. In an embodiment, the slider guide 25 is the standard end portion of the tibial alignment guide 20. In another embodiment, as shown in FIGS. 3 to 5, the slider guide 25 may be realisably connected to the rod 21, and may be an add-on feature to repurpose the tibial guide assembly 20 in the gap balancing assembly. In an embodiment, a connector 26 may be defined at a bottom end of the slider guide 25. The connector 26 is shown as being a female connector. However, other arrangements are considered, such as having a male connector. For example, a slider guide 25 or a stem of the tibial alignment plateau 30 may be slidingly inserted into a hole in the rod 21, or any other sliding joint configuration may be present. It is also considered to clip the tibial alignment plateau 30 to the end of the rod 21, in an embodiment using patient specific manufacturing. In yet another variant, the tibial guide assembly 20 and the tibial alignment plateau 30 are a single piece, for example fabricated using 3D printing techniques.

In an embodiment, the slider guide 25 has a shaft 27 that will operatively engage thereon the tibial alignment plateau 30. As observed, the shaft 27 may have non-circular cross-section. It is desired that the tibial alignment plateau 30 be constrained to movement in one translational degree of freedom while assembled in the manner shown in FIGS. 3 to 5 to the slider guide 25, and the non-circular cross-section may assist. A rotational degree of freedom could also be provided, and a circular cross-section would be contemplated therefor. Therefore, as observed in FIGS. 1 and 2, a vertical position of the tibial alignment plateau 30 on the tibial alignment guide 20 may be adjusted, though this may not be necessary, for instance in the case of patient-specific manufacturing for the tibial alignment guide 20 and tibial alignment plateau 30.

Referring to FIGS. 3 to 5, the tibial alignment plateau 30 is shown in greater details. The expression "plateau" may be interpreted in some variants as representing a plane. The tibial alignment plateau 30 has a plateau portion 31. An under surface of the plateau portion 31 is for example generally flat, or configured for contacting the tibia in a predetermined manner (e.g., contour matching in patient specific manufacturing). The under surface of the plateau portion 31 may be configured for contacting an existing implant, in a procedure in which only the femoral component of the knee joint is revised. The opposing side of the plateau portion 31 may be representative of a tibial plateau from the perspective of a femoral component, and may have surface features thereon as described below. The mechanical axis of the tibia T may be normal to a plane of the plateau portion 31, when the plateau portion 31 is mounted onto the tibial alignment guide 20. The under surface of the plateau portion 31 is designed to abut against a top surface of the tibia T, whether the surface is resected, has an implant, is native. The top surface may be referred to as an articular surface. A slot 32 may be defined in a posterior end of the plateau portion 31. The slot 32 may assist in locating the plateau portion 31 onto the top tibial surface so as to abutingly cover as much of the top tibial surface. If the intramedullary tibial rod 12 is present, the slot 32 receives its end.

Receptacles 33L and 33M may be defined on a medial side and a lateral side of the plateau portion 31. In an embodiment, the receptacles 33L and 33M are depressions in an otherwise flat top surface of the plateau portion 31, the top surface being referred to as a femur-facing surface. The receptacles 33L and 33M may be separated by a surface 33. The surface 33 may be for example flat, and may consequently be oriented with the mechanical axis (or other orientation landmark) generally normal to it (e.g., within 10 degrees in a perpendicular plane), by the abutting relation between the plateau portion 31 and the tibia. For clarity, the affixed letters L and M are used in the present disclosure to relate to the expressions lateral or medial, relative to the standard medio-lateral axis of human anatomy. An arm 34 may project in an anterior direction of the plateau portion 31. The arm 34 has a bore 35 therein. The bore 35 has a shape that is complementary to that of the shaft 27 of the slider guide 25. It is the interaction between the bore 35 and the shaft 27 that results in the transitional joint being formed between the tibial alignment plateau 30 and the tibial alignment guide 20, allowing movement along direction Y (FIG. 4). As mentioned above, the translational joint is optional, as the plateau portion 31 may be without such joint. The tibial alignment plateau 30 may even be an integral part of the tibial alignment guide 20.

Referring to FIGS. 3 and 4, gap spacers 36L and 36M are received in the receptacles 33L and 33M of the tibial alignment plateau 30, respectively. In an embodiment, the gap spacers 36L and 36M are made of a material that exhibits low friction. The gap spacers 36 (i.e., concurrently referred to as gap spacers 36) may come in various thicknesses. For clarity, the expression "thickness" is used to express the distance of the gap spacers 36 from a contact surface with the tibial plateau 31 to a top surface that will contact the femur F as described below. The gap spacers 36L and 36M may be of the same thickness or may have different thicknesses, so as to define a thickness profile. The thickness profile may be a projection of the gap spacers 36 (or equivalent gap spacer portion) on a frontal plane of the tibia, with an outline of a top surface of the gap spacers defining the thickness profile. The gap spacers 36 are removably insertable in the receptacles 33L and 33M. In an embodiment, the contours of the receptacles 33L and 33M hold the spacers 36 captive therein. However, other configurations may be used for the spacers 36 to be connected to the plateau portion 31. In an embodiment, pins or like male connectors project from the plateau portion 31, with corresponding holes or like female connectors in the spacers 36, or vice versa. In another embodiment, the gap spacers 36 are integrally formed in the plateau portion 31. In such a case, a user may be provided with a plurality of plateau portions 31 with different sizes of gap spacers 36.

Referring to FIGS. 3 and 4, the tibial alignment plateau 30 is shown as being used. In such circumstances, the tibial alignment plateau 30 is attached to the tibial alignment guide 20, such as by being slidingly mounted onto the slider guide 25 of the tibial alignment guide 20. The tibial alignment plateau 30 comes into contact with the top surface of the tibia T and may be said to have the mechanical axis of the tibia T normal to its plane when contacting the tibia T. In an embodiment, the tibial alignment plateau 30 is placed onto the top surface of the tibia T without the presence of the tibial alignment guide 20. For instance, the tibia T has an implant already (e.g., not being revised), native bone, or an already resurfaced plateau. The tibial alignment plateau 30 may have orientation landmark(s) to be properly oriented on the tibia T. One such orientation landmark may be a patient specific surface applying against a non-resected contour of the bone. The gap spacers 36 may be interchanged by an operator so as to see the impact of the tension in the ligaments on opposite sides of the gap between tibia T and femur F, in an operation known as soft tissue balancing. This may be done when the knee is in flexion as in FIGS. 1 to 4. A slight rotating movement of the tibia T may be performed relative to the femur F to allow an operator to observe the tension in the ligaments. It is through these movements that the balancing of the soft tissue may be achieved by observation of the tension, by palpation for example. An unbalance may prompt the change of one or both gap spacers 36. As an example, a lack of tension on the medial side may require a user to use a thicker gap spacer 36M. This iterative process may be repeated until suitable soft tissue balance has been achieved. Such soft tissue balance may result in a transepicondylar axis being generally parallel to a plane of the plateau portion 31 and thus to a plane of the tibial component of the knee implant. FIGS. 7A to 7D show a plurality of such sets of gap spacers 36 along with series of changes in a position of a transepicondylar axis TEA as a function of the thickness of the gap spacers 36. In cases of significant bone loss from removal of the existing primary implant, the transepicondylar axis TEA may be determined through a registration of the femur to a virtual 3D model of the patient's femur based on preoperative planning using appropriate imagery.

Once suitable soft tissue balance has been achieved, it is desired to adjust an orientation of the femoral cut guide 10 relative to the femur F, so as to subsequently perform cuts of the femur F with the femoral cut guide 10, which cuts are aligned with the soft tissue balancing achieved. For this purpose, a cut guide alignment spacer 40 as shown in FIGS. 6 and 7A-7D may be used. The cut guide alignment spacer 40 is shown as being physically separate from the tibial alignment plateau 30, but may be integrated to the tibial alignment plateau 30. The cut guide alignment spacer 40 has a spacer member 41. The spacer member 41 is designed to be lodged between the plateau portion 31 and the femoral cut guide 10. As the femoral cut guide 10 may be rotated relative to the intramedullary femoral rod 11, the femoral cut guide 10 may be rotated to be flat against the spacer member 41, consequently aligning its orientation to a plane of the plateau portion 31. For this reason, the spacer member 41 may have a slot 42. The slot 42 may be used to receive in it the end of the intramedullary tibial rod 12 that may project upwardly from the tibia T, if present. The spacer member 41 has a femoral contact surface 43 and a tibial contact surface 44. The femoral contact surface 43 and the tibial contact surface 44 may or may not be parallel to one another. The spacer member 41 may be selected as a function of the identity of the gap spacers 36L and 36M. More particularly, as the gap spacers 36L and 36M may be of different thicknesses, it is desired to have a slope of the femoral contact surface 43 relative to the tibial contact surface 44 to emulate the spacing between femur F and tibia T that is dictated by the size of the gap spacers 36L and 36M. To this end, indicia may be provided on the spacer member 41 or on a handle 45 of the cut guide alignment spacer 40 to indicate the size of the spacer member 41. The handle 45 may be present so as to facilitate the lodging of the spacer member 41 in the gap between the femur F and the tibia T. So as to reduce an inventory of the cut guide alignment spacer 40, it may be desired to have another spacer member 46 at the other end, with the spacer member 46 having a different geometry than the geometry of spacer member 41, i.e., the spacer member 46 being sized for a different pair of the spacer member 41.

Referring to FIGS. 7A to 7D, it is observed that the gap spacers 36L and 36M come in different sets. This therefore entails that the spacer member 41 is sized so as to perfectly fit between the gap left between the gap spacers 36M and 36L. The femoral cut guide 10 may therefore be rotated to be flat against the femoral contact surface 43, while the tibial contact surface 44 is flat against the plateau portion 31. The femoral cut guide 10 may therefore be locked at the achieved orientation, for cutting implements to then be used to resect the femur F while preserving the orientation achieved using the gap balancing assembly. In the figures, a base of the cut guide 10 is shown, with implement(s) being added on the cut guide to perform the cut planes. The implement(s) may allow a five-plane cut to be made, for example.

The gap balancing assembly may include one or more of the tibial alignment plateau 30 and the cut guide alignment spacer 40, for instance with gap spacers integral to the tibial alignment plateau 30, or a gap spacer portion with a given thickness profile. In another embodiment, the gap balancing assembly may also include a plurality of the cut guide alignment spacer 40 along with different gap spacers 36L and 36M. The gap balancing assembly may also include the slider guide 25 and, optionally, the tibial alignment guide 20. One or more of the components described above may be patient specific. For example, tibial alignment plateau 30 may be a patient specific component while other components are stock. Other arrangements are contemplated.

According to an embodiment, a method for using a gap balancing assembly, such as the one described herein may include one or more of: abutting or placing the tibial alignment plateau 30 against the tibia T while the tibial alignment plateau 30 is in a given orientation relative to the tibia T. The given orientation may be defined in an example as having a mechanical axis of the tibial being normal to a plane of the tibial alignment plateau 30. The tibial alignment plateau 30 may not necessarily be a sliding member but may be an implement that is abutted against the tibial plateau. Gap spacers 36 may be interchanged relative to the tibial alignment plateau 30 while soft tissue balance is assessed. In an embodiment, the gap spacers 36 are modified individually, while in another embodiment, it is the whole tibial alignment plateau 30 that is changed in that it may come in different sizes. The interchange may be repeated until a suitable soft tissue balance is achieved. A cut guide alignment spacer 40 may then be inserted in a gap between the gap spacers 36L and 36M. The cut guide alignment spacer 40 is selected as a function of the thickness of the gap spacers 36L and 36M. An orientation of the femoral cut guide 10 relative to the femur (e.g., the mechanical axis of the femur, via the intramedullary femoral rod 11) is adjusted so as to come into a planar contact with a femoral contact surface 43 of the cut guide alignment spacer 40. In such a step, the transepicondylar axis TEA is set. The femoral cut guide 10 may be locked into place, and the femoral resection may be performed. This may include performing a posterior cut of the femur that is parallel to the transepicondylar axis TEA. In another embodiment, a method for orienting a femoral cut guide may include: abutting a tibial alignment plateau against a top surface of a tibia with the tibial alignment plateau being in a given orientation relative to the tibia; spacing a femur from the tibial alignment plateau using a medial gap spacer and a lateral gap spacer to achieve a desired soft tissue balance, the desired soft tissue balance being indicate of a desired transepicondylar axis; and orienting a femoral cut guide to the desired transepicondylar axis.

In an embodiment, the gap balancing assembly may be described as including the tibial alignment plateau 30 adapted to abut against a top tibial surface in a given orientation, the tibial alignment plateau 30 having a surface aligned with the given orientation, and gap spacers adapted to space a top tibial surface from a femur; and a cut guide alignment spacer 40 having a spacer member with a tibial contact surface for being abutted against said surface of the tibial alignment plateau, and with a femoral contact surface oriented and spaced relative to the tibial contact surface to match a variation between the gap spacers, the femoral contact surface adapted to contact a femoral cut guide to align same with the given orientation.

The gap balancing assembly has been described above as relying on an abutment with the tibial plateau. It is however considered to reverse the gap balancing assembly, by using the alignment plateau 30 against the femur, with the gap spacers 36M and 36L against the articular surface of the tibia, and the cut guide alignment spacer 40 also contacting the articular surface of the tibia. The gap balancing assembly could thus include alignment plateau adapted to abut against an articular surface of a first bone, such as the femur, and one or more gap spacer portions, such as gap spacers, adapted to space the articular surface from a second bone, such as the tibia. The gap spacer portion has a thickness profile as described herein. A spacer member, such as 40, has a first contact surface for being abutted against said alignment plateau, and a second contact surface oriented and spaced relative to the first contact surface to correspond to the thickness profile of the gap spacer portion, the second contact surface adapted to contact a tibial cut guide to align same with the articular surface of the tibia, or a femoral cut guide align same with the articular surface of the femur.

EXAMPLES

The following examples can each stand on their own, or can be combined in different permutations, combinations, with one or more of other examples.

Example 1 is a gap balancing assembly comprising: a tibial alignment plateau adapted to abut against an articular surface of the tibia, and at least one gap spacer portion adapted to space the articular surface from a femur, the at least one gap spacer portion having a thickness profile, and a spacer member having a first contact surface for being abutted against said tibial alignment plateau, and a second contact surface oriented and spaced relative to the first contact surface to correspond to the thickness profile of the at least one gap spacer portion, the second contact surface adapted to contact a femoral cut guide to align same with the articular surface of the tibia.

In Example 2, the subject matter of Example 1 includes, wherein the at least one gap spacer portion is removably connected to the tibial alignment plateau.

In Example 3, the subject matter of Example 2 includes, wherein tibial alignment plateau defines at least one recess to receive the at least one gap spacer portion.

In Example 4, the subject matter of Examples 1 to 3 includes, wherein the at least one gap spacer portion includes a medial gap spacer and a lateral gap spacer.

In Example 5, the subject matter of Example 4 includes, wherein the medial gap spacer and the lateral gap spacer have a different thickness, whereby the thickness profile slopes along a medio-lateral direction relative to the articular surface of the tibia.

In Example 6, the subject matter of Examples 1 to 5 includes, wherein the tibial alignment plateau has a femur-facing surface aligned in a given orientation relative to the tibia.

In Example 7, the subject matter of Example 6 includes, wherein a mechanical axis of the tibia is normal to the femur-facing surface in the given orientation.

In Example 8, the subject matter of Examples 6 and 7 includes a tibial alignment guide configured to be mounted to the tibia relative to the given orientation, the tibial alignment plateau connected to the tibial alignment guide.

In Example 9, the subject matter of Example 8 includes, wherein a shaft of the tibial alignment guide is configured to be generally aligned with a mechanical axis of the tibia.

In Example 10, the subject matter of Examples 8 and 9 includes, wherein the tibial alignment plateau is connected to the tibial alignment guide by a joint defining at least a translational degree of freedom.

In Example 11, the subject matter of Examples 8 to 10 includes, wherein the tibial alignment clamp has an ankle clamp.

In Example 12, the subject matter of Examples 1 to 11 includes, wherein the spacer member is separate from the tibial alignment plateau.

In Example 13, the subject matter of Example 12 includes, wherein the first contact surface and the second contact surface of the spacer member are planar.

In Example 14, the subject matter of Example 13 includes, wherein the first contact surface and the second contact surface of the spacer member are non-parallel to one another.

In Example 15, the subject matter of Example 1 includes, wherein an under surface of the tibial alignment plateau has a contour-matching surface portion configured to negatively match a surface of the tibia for complementary unique engagement.

Example 16 is a system comprising: the gap balancing assembly according to any one of Examples 1 to 15; and a femoral cut guide.

In Example 17, the subject matter of Example 16 includes a member configured to be secured to the femur, and a joint between the member and the femoral cut guide, the joint providing at least one rotational degree of freedom.

In Example 18, the subject matter of Example 17 includes, wherein the joint is a spherical joint.

Example 19 is a method for orienting a femoral cut guide comprising: abutting a tibial alignment plateau against an articular surface of a tibia; spacing a femur from the tibial alignment plateau using at least one gap spacer portion having a thickness profile to achieve a desired soft tissue balance, the desired soft tissue balance being indicative of a desired transepicondylar axis; and orienting a femoral cut guide to the desired transepicondylar axis as a function of the thickness profile.

In Example 20, the subject matter of Example 19 includes, wherein abutting the tibial alignment plateau and spacing the femur are repeated with the tibial alignment plateau having different ones of the thickness profile.

In Example 21, the subject matter of Example 20 includes, wherein abutting the tibial alignment plateau and spacing the femur are repeated by changing a medial gap spacer and/or a lateral gap spacer concurrently defining the at least one gap spacer portion.

In Example 22, the subject matter of Examples 19 to 21 includes, wherein orienting the femoral cut guide includes inserting a spacer member corresponding to the thickness profile between the tibial alignment plateau and the femoral cut guide.

In Example 23, the subject matter of Examples 19 to 22 includes, wherein abutting the tibial alignment plateau includes mounting a tibial alignment guide to the tibia, the tibial alignment plateau being connected to the tibial alignment guide.

In Example 24, the subject matter of Example 23 includes, wherein mounting the tibial alignment guide to the tibia includes aligning the tibial alignment guide with a mechanical axis of the tibial.

In Example 25, the subject matter of Example 24 includes, wherein abutting the tibial alignment plateau includes abutting the tibial alignment plateau with the mechanical axis being generally normal to the tibial alignment plateau.

In Example 26, the subject matter of Examples 23 to 25 includes, wherein abutting the tibial alignment plateau includes sliding the tibial alignment plateau along the tibial alignment guide.

In Example 27, the subject matter of Examples 19 to 26 includes, wherein abutting the tibial alignment plateau against the articular surface of the tibia includes abutting the tibial alignment plateau against an implant on the tibia.

In Example 28, the subject matter of Examples 19 to 27 includes resecting the femur to form at least one plane aligned with the desired transepicondylar axis.

Example 29 is a gap balancing assembly comprising: an alignment plateau adapted to abut against an articular surface of a first bone, and at least one gap spacer portion adapted to space the articular surface from a second bone, the at least one gap spacer portion having a thickness profile, and a spacer member having a first contact surface for being abutted against said alignment plateau, and a second contact surface oriented and spaced relative to the first contact surface to correspond to the thickness profile of the at least one gap spacer portion, the second contact surface adapted to contact a cut guide to align same with the articular surface of the first bone.

In Example 30, the subject matter of Example 29 includes, wherein the first bone is a femur and the second bone is a tibia.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A gap balancing assembly comprising: a femoral cut guide configured to be connected to a femur and rotatable relative to the femur, a tibial alignment plateau adapted to abut against an articular surface of the tibia, and at least one gap spacer portion adapted to space the articular surface from the femur, the at least one gap spacer portion having a thickness profile, a spacer member having a first contact surface for being abutted against said tibial alignment plateau, and a second contact surface oriented and spaced relative to the first contact surface, the second contact surface adapted to contact the femoral cut guide to align same with the articular surface of the tibia, wherein the femoral cut guide is rotated relative to the femur to abut against the second contact surface of the spacer member, and a member configured to be secured to the femur, and a joint between the member and the femoral cut guide, the joint providing at least one rotational degree of freedom.

2. The gap balancing assembly according to claim 1, wherein the at least one gap spacer portion is removably connected to the tibial alignment plateau.

3. The gap balancing assembly according to claim 2, wherein tibial alignment plateau defines at least one recess to receive the at least one gap spacer portion.

4. The gap balancing assembly according to claim 1, wherein the at least one gap spacer portion includes a medial gap spacer and a lateral gap spacer.

5. The gap balancing assembly according to claim 4, wherein the medial gap spacer and the lateral gap spacer have a different thickness, whereby the thickness profile slopes along a medio-lateral direction relative to the articular surface of the tibia.

6. The gap balancing assembly according to claim 1, wherein the tibial alignment plateau has a femur-facing surface aligned in a given orientation relative to the tibia.

7. The gap balancing assembly according to claim 6, wherein a mechanical axis of the tibia is normal to the femur-facing surface in the given orientation.

8. The gap balancing assembly according to claim 6, including a tibial alignment guide configured to be mounted to the tibia relative to the given orientation, the tibial alignment plateau connected to the tibial alignment guide.

9. The gap balancing assembly according to claim 8, wherein a shaft of the tibial alignment guide is configured to be generally aligned with a mechanical axis of the tibia.

10. The gap balancing assembly according to claim 8, wherein the tibial alignment plateau is connected to the tibial alignment guide by a joint defining at least a translational degree of freedom.

11. The gap balancing assembly according to claim 8, wherein the tibial alignment clamp has an ankle clamp.

12. The gap balancing assembly according to claim 1, wherein the spacer member is separate from the tibial alignment plateau.

13. The gap balancing assembly according to claim 12, wherein the first contact surface and the second contact surface of the spacer member are planar.

14. The gap balancing assembly according to claim 13, wherein the first contact surface and the second contact surface of the spacer member are non-parallel to one another.

15. The gap balancing assembly according to claim 1, wherein an under surface of the tibial alignment plateau has a contour-matching surface portion configured to negatively match a surface of the tibia for complementary unique engagement.

16. The gap balancing assembly according to claim 1, wherein the joint is a spherical joint.

17. The gap balancing assembly according to claim 1, wherein the member is an intramedullary rod.

* * * * *